(12) United States Patent
Chen et al.

(10) Patent No.: US 8,050,382 B2
(45) Date of Patent: *Nov. 1, 2011

(54) SAMPLE MODULE WITH SAMPLE STREAM SPACED FROM WINDOW, FOR X-RAY ANALYSIS SYSTEM

(75) Inventors: Zewu Chen, Schenectady, NY (US); Rory Delaney, Burnt Hills, NY (US); Kai Xin, Wynantskill, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 139 days.

This patent is subject to a terminal disclaimer.

(21) Appl. No.: 12/391,677

(22) Filed: Feb. 24, 2009

(65) Prior Publication Data
US 2009/0213988 A1    Aug. 27, 2009

Related U.S. Application Data

(60) Provisional application No. 61/031,148, filed on Feb. 25, 2008.

(51) Int. Cl.
*G01N 23/223* (2006.01)
(52) U.S. Cl. .................................................. 378/47
(58) Field of Classification Search .............. 378/44, 378/47, 208
See application file for complete search history.

(56) References Cited

U.S. PATENT DOCUMENTS

| | | | |
|---|---|---|---|
| 3,980,882 A | 9/1976 | Carr-Brion et al. | |
| 7,072,439 B2 | 7/2006 | Radley et al. | |
| 7,477,724 B2 * | 1/2009 | Meier et al. | 378/45 |

FOREIGN PATENT DOCUMENTS

| | | |
|---|---|---|
| EP | 0916940 B1 | 9/2004 |
| EP | 1482302 A1 | 12/2004 |
| JP | 11-211679 A | 8/1999 |

OTHER PUBLICATIONS

PCT International Search Report and Written Opinion of the International Searching Authority for International Application No. PCT/US2009/034982, dated Oct. 15, 2009.

* cited by examiner

*Primary Examiner* — Jurie Yun
(74) *Attorney, Agent, or Firm* — Jeffrey Klembczyk, Esq.; Kevin P. Radigan, Esq.; Heslin Rothenberg Farley & Mesiti P.C.

(57) ABSTRACT

An x-ray analysis system with an x-ray source for producing an x-ray excitation beam directed toward an x-ray analysis focal area; and a sample chamber for presenting a fluid sample to the x-ray analysis focal area. The x-ray excitation beam is generated by an x-ray engine and passes through an x-ray transparent barrier on a wall of the chamber, to define an analysis focal area within space defined by the chamber. The fluid sample is presented as a stream suspended in the space and streaming through the focal area, using a laminar air flow and/or pressure to define the stream. The chamber's barrier is therefore separated from both the focal area and the sample, resulting in lower corruption of the barrier.

20 Claims, 5 Drawing Sheets

SAMPLE MODULE WITH SAMPLE STREAM SPACED FROM WINDOW, FOR X-RAY ANALYSIS SYSTEM

CROSS-REFERENCE TO RELATED PATENT APPLICATION

This application claims the benefit of U.S. provisional patent application Ser. No. 61/031,148, filed Feb. 25, 2008, which is hereby incorporated herein by reference in its entirety.

TECHNICAL FIELD

This invention relates in general to apparatus and methods used for x-ray analysis of sample streams. More particularly, the present invention is directed to a sample handling apparatus for presenting a suspended sample stream to an x-ray analysis focal area.

BACKGROUND OF THE INVENTION

X-ray analysis of samples is a growing area of interest across many industries such as medical, pharmaceutical, and petroleum. The use of x-ray fluorescence, x-ray diffraction, x-ray spectroscopy, x-ray imaging, and other x-ray analysis techniques has led to a profound increase in knowledge in virtually all scientific fields.

U.S. Pat. Nos. 6,934,359 and 7,072,439, incorporated by reference herein in their entirety and assigned to X-Ray Optical Systems, Inc., the assignee of the present invention, disclose monochromatic wavelength dispersive x-ray fluorescence (MWD XRF) techniques and systems for the analysis of liquid samples. Moreover, commonly assigned U.S. Pat. No. 7,277,527 (also included by reference in its entirety) entitled "Movable Transparent Barrier for X-Ray Analysis of a Pressurized Sample" addresses a particular problem inherent in moving sample streams as discussed further below.

X-ray fluorescence (XRF) is an analytical technique by which a substance is exposed to a beam of x-rays to determine, for example, the presence of certain components. In XRF, at least some of the chemical constituents of the substance exposed to x-rays can absorb x-ray photons and produce characteristic secondary fluorescence. These secondary x-rays are characteristic of the chemical constituents in the substance. Upon appropriate detection and analysis these secondary x-rays can be used to characterize one or more of the chemical constituents. XRF techniques have broad applications in many chemical and material science fields, including industrial, medical, semiconductor chip evaluation, petroleum, and forensics, among others.

As one particular example, these patents disclose techniques for the determination of the level of sulfur in petroleum fuels, and a commercialized analyzer (SINDIE) is now in widespread use for this measurement at petroleum refining, pipeline, and terminal facilities.

XRF techniques can be used for this application (as discussed above and throughout the above-incorporated patents). The basic technique involves exciting a fuel sample with x-rays and examining the fluorescence emitted. Each element emits a unique spectral signature. A detector then measures the wavelengths of the emitted x-rays, and software can reduce this measured spectrum to a weighted composition of the sulfur in the sample.

XRF fluid testing can take place off-line, i.e., using a bench-top, laboratory-type instrument to analyze a sample. The material is removed from its source (e.g., for fuel, from a refinery or transportation pipeline) and then simply deposited in a sample chamber. Off-line, bench-top instruments need not meet any unusual operational/pressure/environmental/size/weight/space/safety constraints, but merely need to provide the requisite measurement precision for a manually-placed sample. Moreover, off-line instruments can be easily maintained between measurements.

In contrast to off-line analysis, on-line analysis provides "real-time" monitoring of sample composition at various points in the manufacturing process. For example, all fuel products are subject to sulfur level compliance—requiring some variant of on-line monitoring during fuel refining and transportation in pipelines. On-line analysis of fuels in a refinery and in pipelines, however, requires consideration of numerous operational issues not generally present in an off-line, laboratory setting. A fully automated fuel sample handling system is required—with little or no manual intervention or maintenance. Also, since fluids are usually under pressure in pipelines, any sample handling system must account for pressure differentials. This is especially important since certain portions of XRF x-ray "engines" (discussed further below) operate in a vacuum. Also, the instrument's electronics require packaging in an explosion-proof housing—separate from the sample handling system.

In this application, therefore, one of the most critical components is the sample barrier(s) which allow photons of x-rays to excite sulfur atoms in the fluid, and photons emitted from the atoms to be counted at the engine's detector, while at the same time maintaining the vacuum in the x-ray engine and the pressure of the fluid. X-ray stimulation creates sulfur ionization and adsorption at this interface over time and on certain types of barrier materials—leading to undesired sulfur residue and degradation of the barrier's x-ray transparency. More generally, many XRF applications require a barrier to protect the engine from any number of adverse interface effects from the sample material and/or the measurement environment.

The barrier system of above-incorporated U.S. Pat. No. 7,277,527 offered a very important and successful solution to these problems in the form of a moveable barrier advanced at programmable intervals to clean portions of a window roll. This technique, though successful and very functional in the field, has certain limitations, including the need to advance rolled, barrier material periodically using a mechanical system of rolls, motors, and controls.

What is required, therefore, is a lower cost and lower maintenance barrier technique and apparatus for an on-line x-ray analysis system, which protects the x-ray engine from adverse sample and environmental effects, while maintaining the integrity and transparency of the interface to the sample for accurate measurements without excessive moving parts.

SUMMARY OF THE INVENTION

The shortcomings of the prior art are overcome and additional advantages are provided by the present invention which in one aspect is an x-ray analysis sample handling apparatus with a chamber for presenting a fluid sample to an x-ray analysis focal area of an x-ray engine. The x-ray analysis focal area is disposed within space defined by the chamber. The apparatus presents the fluid sample as a stream, suspended in the space defined by the chamber, and streaming through the focal area.

The stream may be suspended in the chamber by supplying a pressurized fluid sample to the chamber and/or by an air flow supplied to the chamber and defining the stream.

The sample handling apparatus may be combined with an x-ray analysis system, the x-ray fluorescence system comprising the x-ray engine including an x-ray excitation path, and an x-ray detection path. The x-ray excitation and/or the x-ray detection paths together may define the x-ray analysis focal area in the chamber.

The focal area may be a focal point defined by focused x-rays to/from a focusing optic in the x-ray excitation path and/or the x-ray detection path. The focusing optic may be a curved diffracting optic, polycapillary optic, or focusing monochromatic optic. The focusing monochromatic optic could be a doubly curved crystal optic or doubly curved multi-layer optic. The focusing optic in the x-ray detection path may be positioned such that an input focal point thereof is at the x-ray focal point, and corresponds to an output focal point of at least one focusing optic in the x-ray excitation path.

The fluid sample may comprise a petroleum-based product requiring the measurement of an analyte, such as sulfur or chlorine. The apparatus may also include an x-ray transparent barrier in a wall of the chamber for allowing x-rays to/from the focal area, the barrier being separated from the fluid sample stream such that the fluid does not continuously contact the barrier.

The sample handling apparatus of the present invention maintains a clear sample barrier (e.g., window), requires no moving parts, and can be provided at a lower cost both initially and throughout its maintenance lifetime.

Further, additional features and advantages are realized by the techniques of the present invention. Other embodiments and aspects of the invention are described in detail herein and are considered a part of the claimed invention.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in combination with the accompanying drawings in which:

BEST MODE FOR CARRYING OUT THE INVENTION

Figure 1:
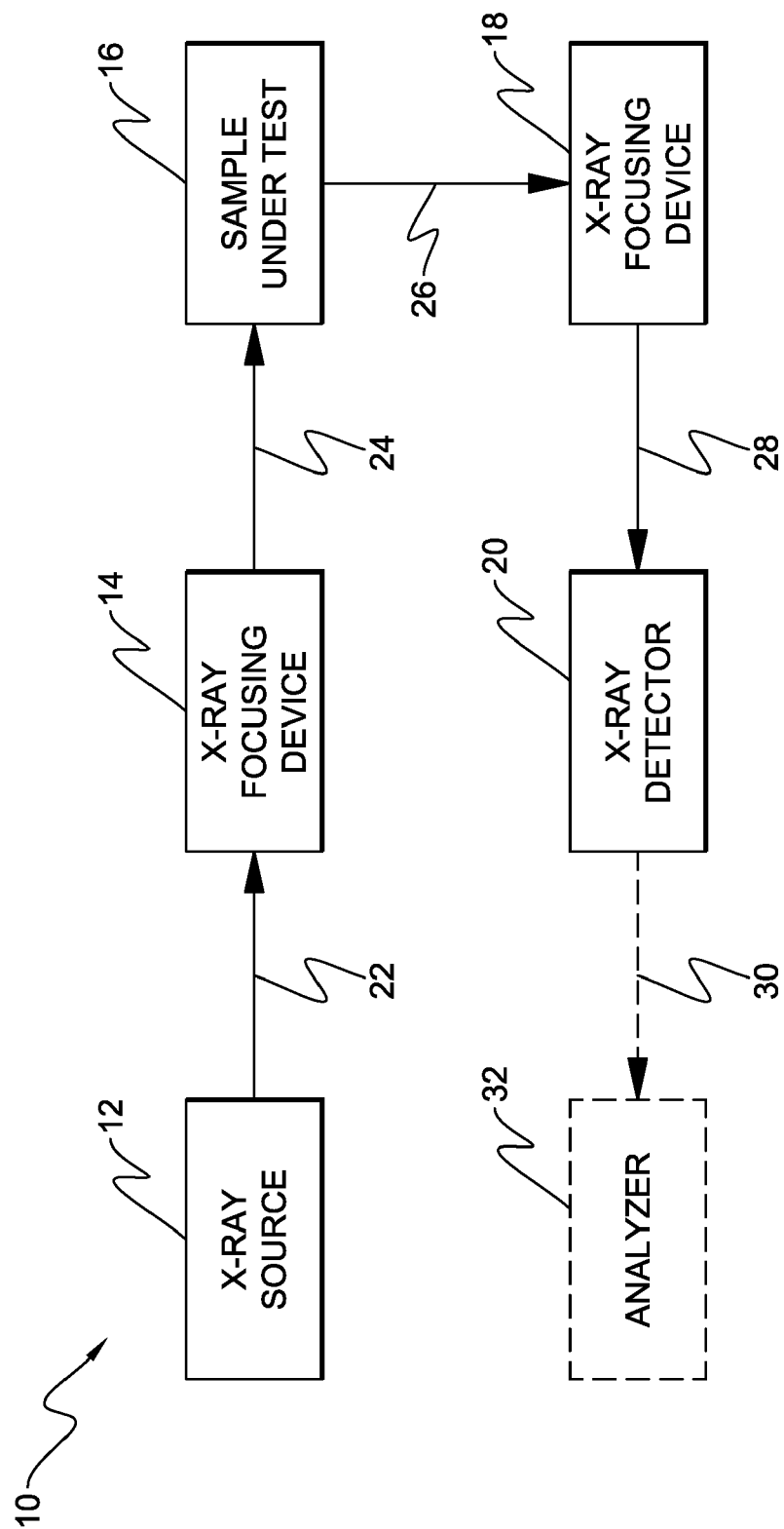
FIG. 1 is a functional block diagram of the elements of an exemplary x-ray fluorescence system.

Presented herein is a technique for handling a fluid sample as it is analyzed in an x-ray analysis system. FIG. 1 is a functional block diagram of a typical x-ray system 10 used for exposing a sample to x-ray radiation to produce fluorescent radiation which can then be detected and analyzed to determine a characteristic of the sample. The system typically includes an x-ray source 12, a first x-ray focusing device 14, a sample chamber 16, a second x-ray focusing device 18, and an x-ray detector 20. The x-ray source 12, for example, an x-ray tube, produces a beam of x-rays 22. Though x-rays are used throughout the specification, the invention extends to neutron, particle-beam or gamma ray radiation. Beam 22 may diffracted or focused by means of one or more x-ray focusing optics 14 as discussed further below.

The sample under test in sample chamber 16 may be any desired substance for which a characteristic measurement is desired. If the sample is static (in, for example, an off-line system), the sample is typically located on a relatively flat surface, for example, an x-ray reflective flat surface or an optically-reflective surface. The sample, if a solid, liquid, or gas, may also be contained in a closed container or chamber, for example, a sealed container, having a x-ray transparent aperture through which x-ray beam can pass. The present invention is directed to, in general, samples in fluid form (e.g., particulate, liquid, gas, or a liquid-based material (e.g. slurry with particulate matter)) moving in the chamber or under pressure in the chamber, or exerting some other potentially disruptive forces or effects within the chamber.

When irradiated by beam 24, at least one of the constituents of sample in chamber 16 is excited in such a fashion that the constituent fluoresces, that is, produces a secondary source of x-rays 26 due to excitation by x-rays 24. Again, since x-ray beam 26 is typically a diverging beam of x-rays, beam 26 is focused by means of the second x-ray focusing device 18, for example, a device similar to device 14, to produce a focused beam of x-rays 28 directed toward x-ray detector 20. It will be apparent to those skilled in the art that this and other aspects of the present invention, though described with respect to x-ray fluorescence applications, may also be utilized in x-ray diffraction, particle-beam, neutron or gamma ray applications.

X-ray detector 20 may be, e.g., a proportional counter-type or a semiconductor type x-ray detector. Typically, x-ray detector 20 produces an electrical signal 30 containing at least some characteristic of the detected x-rays which is forwarded to an analyzer 32 for analysis, printout, or other display.

Figure 2:
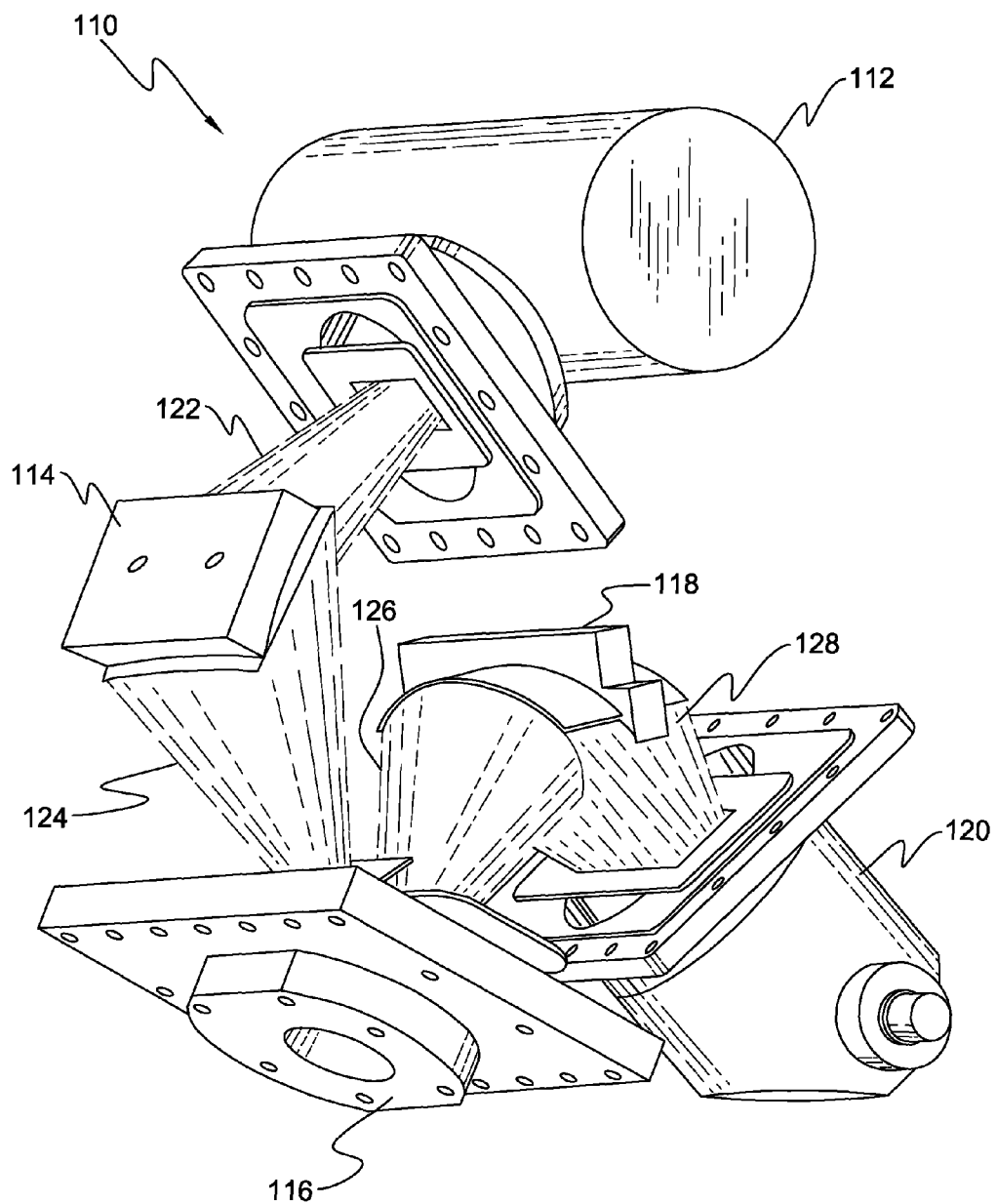
FIG. 2 is an isometric view of an exemplary x-ray fluorescence source/detection "engine" with an exemplary sample chamber.

FIG. 2 illustrates an x-ray fluorescence assembly 110 according to the above-incorporated U.S. Pat. No. 7,072,439 entitled "X-Ray Tube and Method and Apparatus for Analyzing Fluid Streams Using X-Rays." This is an example of a sulfur in fuels analysis system, and also employing the principles of monochromatic X-Ray excitation and collection as set forth in the above-incorporated U.S. Pat. No. 6,934,359 entitled "Wavelength Dispersive XRF System Using Focusing Optic for Excitation and a Focusing Monochromator for Collection." X-ray fluorescence assembly 110 (shown with its housing removed) comprises an x-ray source assembly 112, a sample chamber assembly 116 and an x-ray detector assembly 120. A curved crystal, monochromating and focusing optic 114 is shown in the excitation path, along with another curved crystal focusing optic 118 in the detection path. X-ray source assembly 112 produces an x-ray beam 122 which is focused by x-ray focusing optic 114 to produce a focused beam 124 on a sample under test in chamber assembly 116. The x-ray fluorescence created by the x-ray irradiation of the sample in sample excitation chamber assembly 116 generates x-ray fluorescent beam 126. Beam 126 is focused by x-ray focusing device 118 to provide a focused x-ray beam 128 which is directed to x-ray detector assembly 120.

In prior art methods of XRF detection, the sample excitation path and detection path are maintained in an inert gas atmosphere, for example, in a helium atmosphere. However, the unavailability of inert gases, especially in remote locations, makes the implementation of these prior art processes inconvenient. In contrast, here the sample excitation path and the detection path may be maintained under vacuum and no inert gas is necessary. For example, the radiation paths of system 110 shown in FIG. 2 may be held under vacuum, for example, at least about 15 torr. The vacuum can be provided by a venturi pump having no moving parts. However, if desired and available, an inert gas such as nitrogen or helium can be introduced and maintained in a housing, for example, under pressure.

The use of a vacuum enclosing the x-ray engine (e.g., source, excitation path, collection path, and detector) leads to certain problems at the sample interface—at the respective focal spots of beams 124 and 126. In FIG. 2, the engine's interface to the sample chamber 116 is not directly shown, but may consist of a beryllium or kapton window barrier—which is strong and has the requisite x-ray transparency. But, additional levels of transparency are required when the sample chamber and its operational environment present certain operational difficulties as discussed above, especially in on-line systems.

Figure 3:
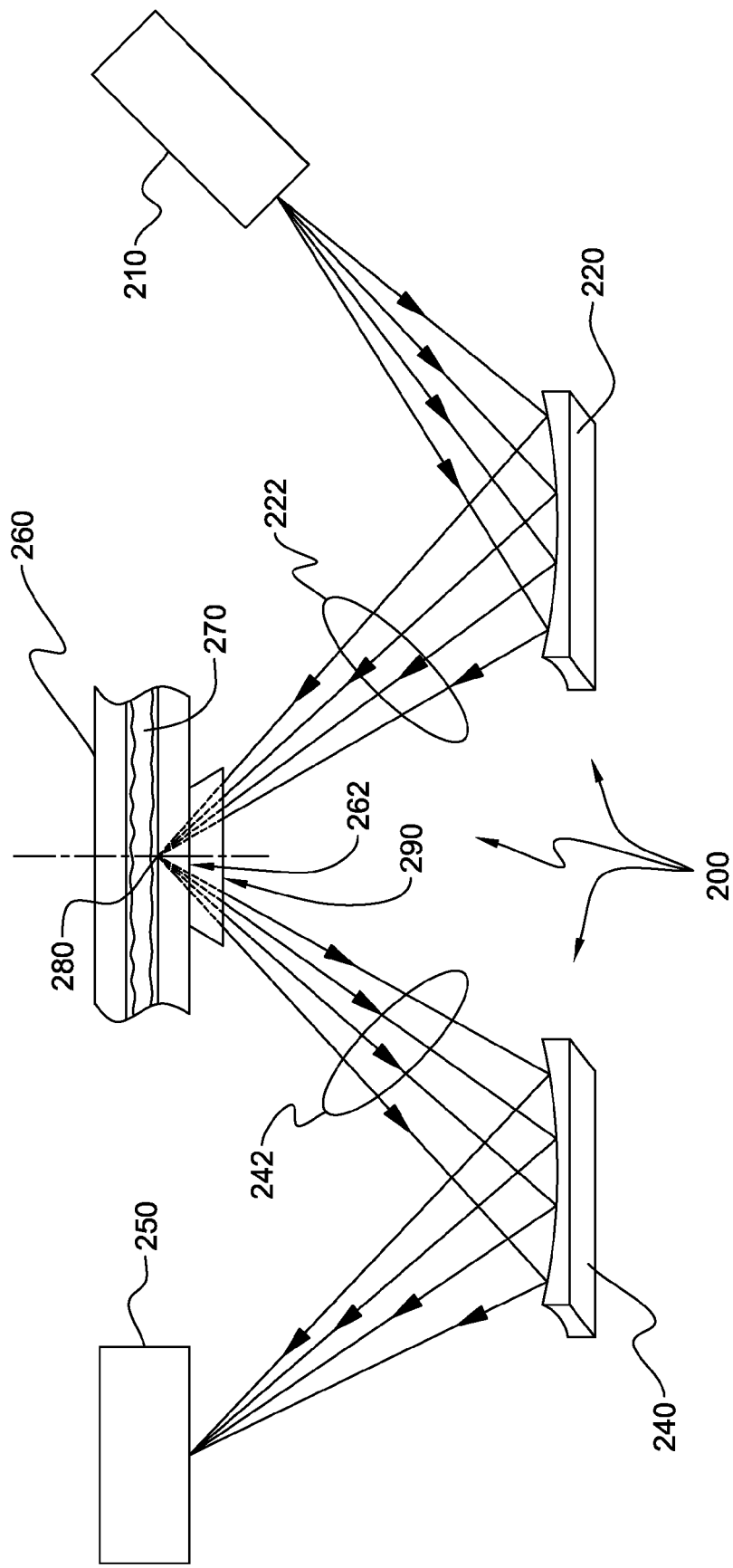
FIG. 3 is a schematic view of an MWD XRF analysis engine in combination with a sample chamber having a suspended sample stream, in accordance with one aspect of the present invention.

In accordance with the present invention, FIG. 3 depicts in schematic view an exemplary MWD XRF x-ray analysis engine 200 in combination with a sample chamber 260. As discussed above, the x-ray analysis engine may involve a focal area (created by excitation and/or detection optics) requiring alignment with the sample in the sample cell. Engine 200 includes, in one embodiment, an x-ray source 210 and detector 250. X-ray optics 220 and/or 240 can be placed in the excitation and/or detection paths of the engine. These optics require a high degree of alignment with the sample focal area to function at the requisite limits of detection discussed above. Such optics include, for example, curved crystal monochromating optics such as those disclosed in commonly assigned U.S. Pat. Nos. 6,285,506; 6,317,483; and 7,035,374; and/or multilayer optics; and/or polycapillary optics such as those disclosed in commonly assigned U.S. Pat. Nos. 5,192,869; 5,175,755; 5,497,008; 5,745,547; 5,570,408; and 5,604,353. Optic/source combinations such as those disclosed in commonly assigned U.S. Pat. Nos. 7,110,506; 7,209,545; and 7,257,193 are also useable. Each of the above-noted patents is incorporated herein by reference in its entirety.

Exemplary curved monochromating optics in the excitation and detection paths are shown in FIG. 3, which is the engine configuration of the SINDIE sulfur analyzer discussed above. However, an optic may only be present in one of these paths, which still requires precise alignment. In one example, an optic of any of the above-described types may only be present in the excitation path, and the detection path would include an energy dispersive detector. This is the common configuration of an energy dispersive x-ray fluorescence (EDXRF) system.

Optic 220 focuses and monochromates the excitation x-rays 222 from the source 210 to a focal area 280 within the sample chamber 260. Optic 240 may also be used to focus the secondary fluorescence x-rays 242 from the focal area 280 to the detector 250. The excitation x-rays 222 and fluorescence x-rays 242 pass through an engine window barrier 290 (e.g., beryllium) and chamber barrier 262 to the focal area 280 within the chamber 260 and through which a sample flows. "Focal area" is used broadly herein to connote a sample analysis area to/from which x-rays are directed. In one embodiment, the focal area could be a small focal point with a diameter between 1-2 mm (or smaller) formed by converging excitation and/or fluorescence x-rays.

Figure 4:
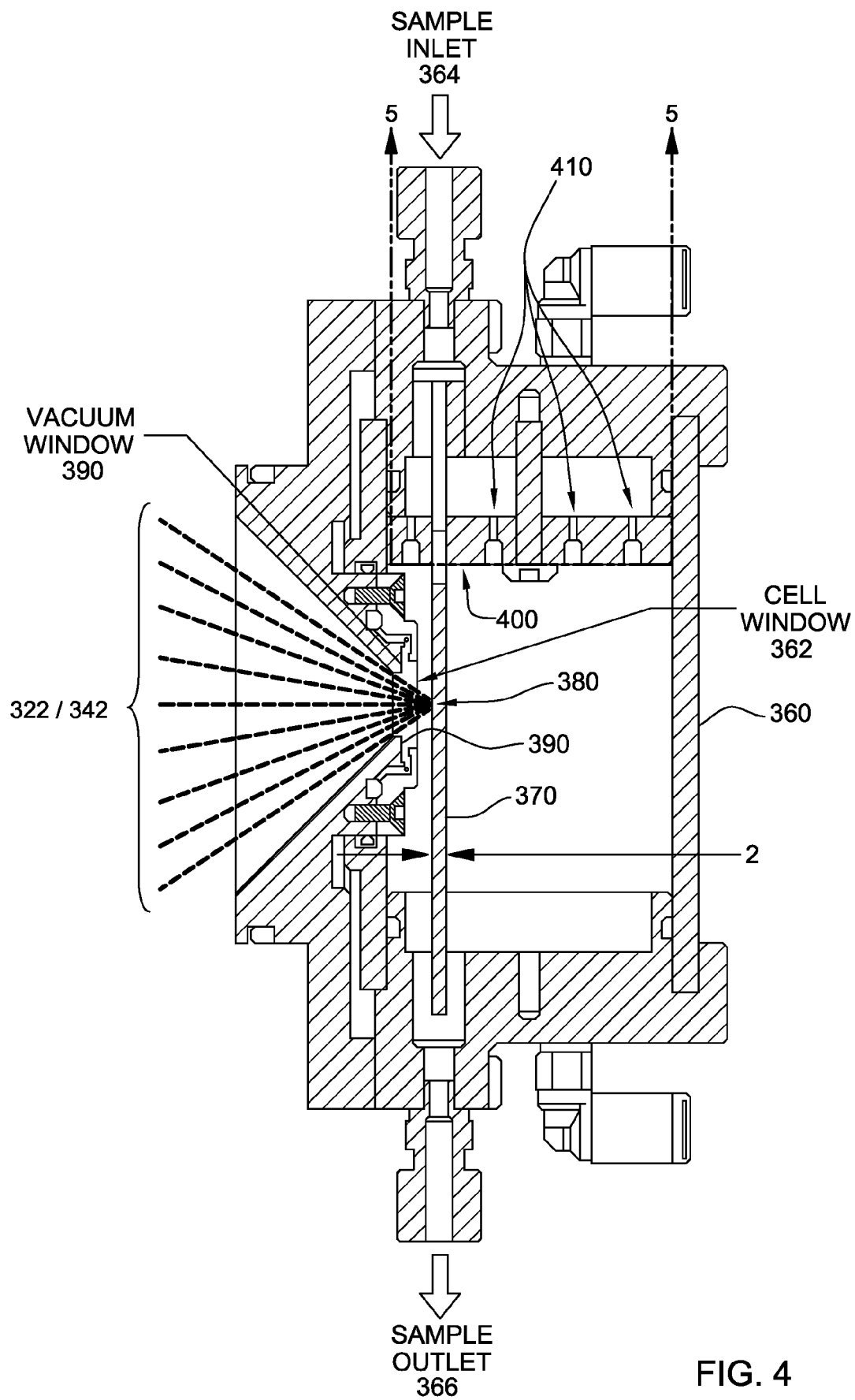
FIG. 4 is a sectional view of an exemplary sample module for an x-ray fluorescence analysis system.

In accordance with the present invention, the fluid sample is presented into the sample chamber as a sample stream 270. The sample stream is suspended within the sample chamber and is spaced apart from the chamber's barrier 262. The sample chamber could be part of a larger flow pipe system, a section of which is depicted in FIG. 3, or could be a relatively confined space as depicted in FIG. 4 below with a sample inlet and outlet. Therefore, the term "sample chamber" is used broadly herein to connote any type of apparatus within which a sample stream can be defined, near the x-ray engine.

FIG. 4 is a sectional view of an exemplary x-ray analysis sample handling apparatus in accordance with the present invention, having a sample chamber 360 with sample stream 370 suspended therein. The sample 370 enters the sample chamber through sample inlet 364 and exits through sample outlet 366. The x-ray excitation path 322 and/or the x-ray detection path 342 define the focal area 380 within the chamber 360. The sample stream 370 streams through the focal area 380. The word "through" is broadly used herein to connote the stream passing directly through the focal area, or proximate thereto, with proximity being adequate enough to create the stimulation and/or fluorescent x-rays as required in a workable x-ray system.

The engine vacuum barrier 390 and chamber barrier 362 are made from x-ray transparent material to allow the x-rays to reach sample stream 370.

In accordance with the present invention, sample stream 370 is spaced apart from chamber barrier 362. Having the chamber barrier spaced apart from the sample stream minimizes any residue on the barrier and allows it to maintain its x-ray transparent qualities.

In one embodiment, flow interface surface 400 depicted in FIG. 4 allows the sample stream 370 to maintain suspension within chamber 360 using continuous "laminar" air flow through conduits 410. The continuous air flow keeps the flow of the sample stream 370 spaced apart from the chamber barrier 362, and can also be used to purge unwanted fumes or other residue created by the sample (either simultaneous with a streaming sample or off-line). In addition, as a simultaneous or separate technique, the sample stream may also be suspended within the sample chamber by applying pressure to the fluid sample as it enters the chamber. A pressurized sample stream can be used in combination with the air flow from the interface or by itself to achieve its suspended nature while in the sample chamber.

This interface surface 400 also allows the sample module to be operated horizontally without compromising the suspended sample stream, i.e., there are no particular orientation requirements of the chamber—if the streaming technique is designed correctly.

Figure 5:
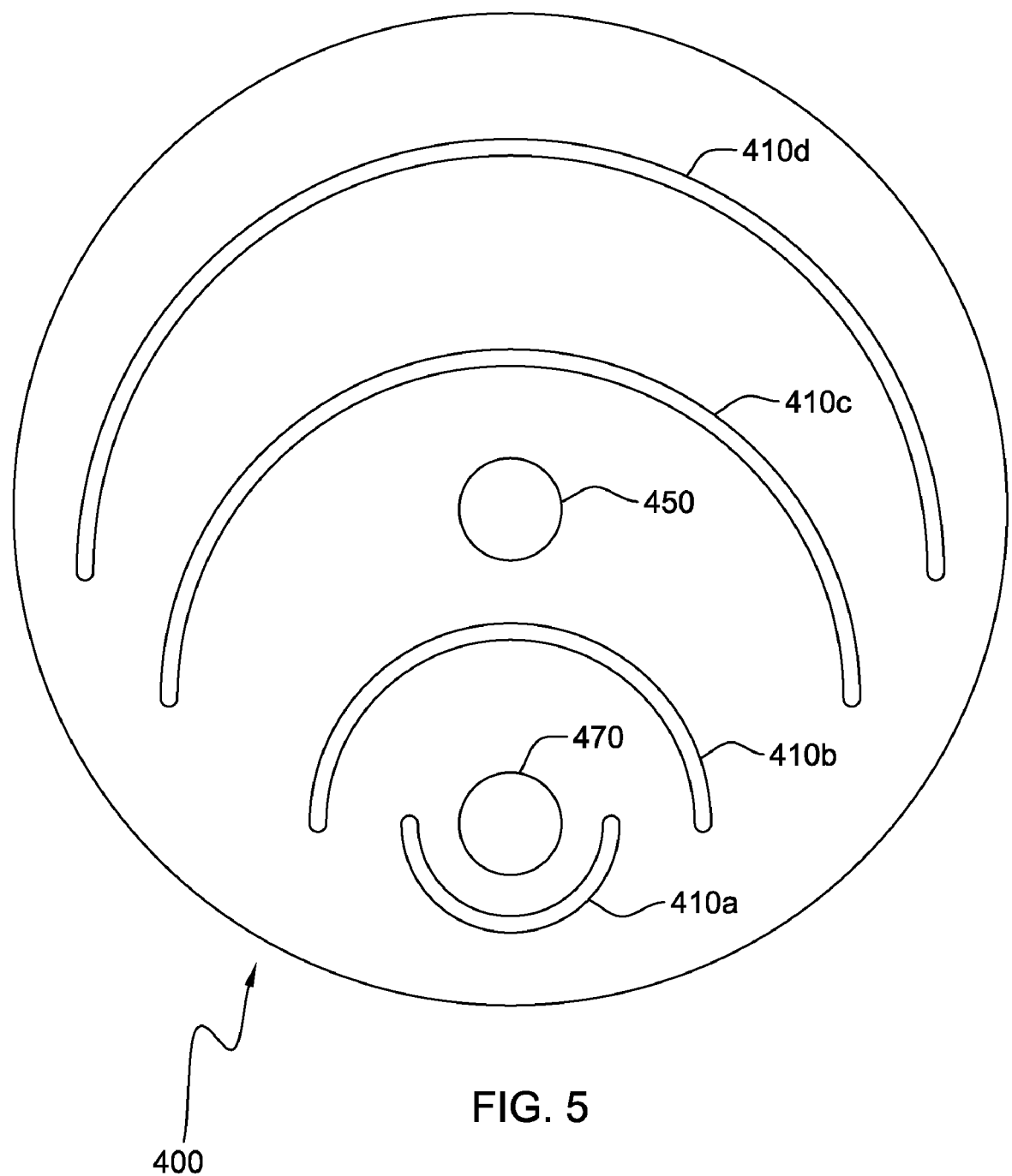
FIG. 5 is a sectional view of a flow interface which controls the flow of air and/or the fluid sample during analysis.

FIG. 5 is a sectional view of flow interface 400. Openings 410a, 410b, 410c, and 410d allow air to enter the sample chamber and are strategically placed to maintain the suspension of the sample stream around its perimeter within the chamber. The air (or nitrogen) can also be used to purge any fumes or residue from the sample chamber. Opening 470 allows the sample stream to enter the sample chamber. Opening 450 allows a fastener for fastening interface 400 within the sample module. In one embodiment this interface 400 can be formed by a plate with openings that can be fastened within the sample chamber.

In one example, the stream is of a diameter of 1-2 mm, which corresponds to the size of the focal point (therefore minimizing the amount of sample in the chamber); and is spaced from the chamber barrier 362 by about 2-3 mm.

The fluid sample is broadly defined herein as any type of streamable material including particulate, liquid, gas, or a liquid-based material (e.g. slurry with particulate matter). This includes any petroleum-based products. This invention is particularly useful for analytes like sulfur and chlorine that are present in petroleum fuels. The inventors recognized that window degradation is a particularly serious problem to address for these analytes.

The present invention provides more accurate analysis results, as follows: (1) Since the barrier remains clean by use of a suspended sample stream, rather than a system involving direct sample/barrier contact, and/or any type of active barrier cleaning/replacement system, there are fewer moving parts which reduces maintenance and cost requirements for the system as well as eliminating a potential cause for system failure. (2) Moreover, having a focal area spaced away from the barrier also reduces the chance for residue build-up as follows: The problems discussed above regarding barrier residue are caused in large part to the x-ray focal area being directly on or near the chamber barrier. This increased the x-ray flux per unit area on the barrier (because of the focusing optics). This increased flux contributed to the rate of residue build-up on the sample barrier. In the present invention (as evident from FIG. 4), the chamber barrier 362 is located in a portion of the x-ray beam 322/342 which has a lower flux-per-area, and is therefore not as highly stimulated by the x-rays, on a per-unit-area basis. And, if any residue does reside on the barrier, it does not have the same interference effect it would have, if the focal point is on the barrier as in the past. The spaced barrier, even if corrupted, therefore does not interfere with the analysis.

Therefore, the present invention provides two simultaneous and important features—it provides a sample spaced from the barrier, along with a focal area spaced from the barrier. Together, these effects reduce the level of residue and also the need for barrier cleaning.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. An x-ray analysis apparatus, comprising:
   an x-ray engine having an x-ray excitation path and an x-ray detection path;
   a chamber for presenting a fluid sample to an x-ray analysis focal area defined by the x-ray engine, the x-ray analysis focal area disposed within space defined by said chamber;
   an x-ray transparent barrier in a wall of the chamber through which both the x-ray excitation and detection paths pass, to and from the focal area, the barrier being separated from the fluid sample such that the fluid does not continuously contact the barrier;
   wherein the x-ray excitation and/or the x-ray detection paths define the x-ray analysis focal area in said chamber; and
   wherein the apparatus presents the fluid sample as a stream, suspended in the space defined by said chamber, and streaming through the focal area.

2. The apparatus of claim 1, wherein the stream is suspended in said chamber by supplying a pressurized fluid sample to said chamber.

3. The apparatus of claim 1, wherein the stream is suspended in said chamber by an air flow supplied to said chamber and defining the stream.

4. The apparatus of claim 1, wherein the focal area is a focal point.

5. The apparatus of claim 4, wherein the focal point is defined by focused x-rays to/from at least one focusing optic in the x-ray excitation path and/or the x-ray detection path.

6. The apparatus of claim 5, wherein the at least one focusing optic is at least one curved diffracting optic or polycapillary optic.

7. The apparatus of claim 5, wherein the at least one focusing optic is at least one focusing monochromatic optic.

8. The apparatus of claim 7, wherein the at least one focusing monochromatic optic is a doubly curved crystal optic or doubly curved multi-layer optic.

9. The apparatus of claim 4, wherein at least one focusing optic in the x-ray detection path is positioned such that an input focal point thereof is at the x-ray focal point, and corresponds to an output focal point of at least one focusing optic in the x-ray excitation path.

10. The apparatus of claim 4, wherein the focal point has a diameter of about 1-2 mm.

11. The apparatus of claim 1, wherein the fluid sample comprises a petroleum-based product requiring the measurement of an analyte therein.

12. The apparatus of claim 11, wherein the analyte is sulfur or chlorine.

13. An x-ray analysis system comprising:
    an x-ray engine having an x-ray source for producing an x-ray excitation beam directed toward an x-ray analysis focal area, and an x-ray detection path for collecting secondary x-rays from the focal area and directing the secondary x-rays toward a detector;
    a sample chamber for presenting a fluid sample to the x-ray analysis focal area, the x-ray analysis focal area disposed within space defined by the chamber; and
    an x-ray transparent barrier on a wall of the chamber through which both the x-ray excitation beam and the secondary x-rays pass;
    wherein the fluid sample is presented as a stream suspended in the space and streaming through the focal area.

14. The system of claim 13, wherein the stream is suspended in said chamber by supplying a pressurized fluid sample to said chamber.

15. The system of claim 13, wherein the stream is suspended in said chamber by an air flow supplied to said chamber and defining the stream.

16. The system of claim 13, wherein the focal area is defined by a focused x-ray excitation beam from at least one focusing optic.

17. The system of claim 16, wherein the at least one focusing optic is a curved diffracting optic or a polycapillary optic.

18. The system of claim 16, wherein the at least one focusing optic is at least one focusing monochromatic optic.

19. The system of claim 18, wherein the at least one focusing monochromatic optic is a doubly curved crystal optic or doubly curved multi-layer optic.

20. The system of claim 16, wherein the focal area is a focal point, and at least one focusing optic in the x-ray detection path is positioned such that an input focal point thereof is at the x-ray focal point, and corresponds to an output focal point of the at least one focusing optic producing the x-ray excitation beam.

* * * * *